(12) United States Patent
Aqad et al.

(10) Patent No.: US 8,956,799 B2
(45) Date of Patent: Feb. 17, 2015

(54) PHOTOACID GENERATOR AND PHOTORESIST COMPRISING SAME

(71) Applicant: Rohm and Haas Electronic Materials LLC, Marlborough, MA (US)

(72) Inventors: Emad Aqad, Northborough, MA (US); Cheng-Bai Xu, Southborough, MA (US); Mingqi Li, Shrewsbury, MA (US); William Williams, III, Ipswich, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 41 days.

(21) Appl. No.: 13/711,679

(22) Filed: Dec. 12, 2012

(65) Prior Publication Data

US 2013/0171567 A1 Jul. 4, 2013

Related U.S. Application Data

(60) Provisional application No. 61/582,341, filed on Dec. 31, 2011.

(51) Int. Cl.
G03F 7/004 (2006.01)
G03F 7/039 (2006.01)
G03F 7/09 (2006.01)

(52) U.S. Cl.
USPC ............ 430/270.1; 430/271.1; 430/919; 430/921; 430/924; 430/925; 549/300; 549/459; 549/473; 549/475; 549/480; 549/493; 549/499; 549/501; 549/504; 562/100; 562/104; 562/105; 562/107; 562/108; 562/109; 562/110; 562/111; 562/113

(58) Field of Classification Search
None
See application file for complete search history.

(56) References Cited

U.S. PATENT DOCUMENTS 7,569,324 B2 8/2009 Kobayashi et al.
2009/0087789 A1* 4/2009 Hirano et al. ............ 430/286.1
2010/0323294 A1 12/2010 Li et al.
2011/0269070 A1 11/2011 Aqad et al.
2013/0084525 A1* 4/2013 Aqad et al. ............... 430/270.1

* cited by examiner

Primary Examiner — Sin J. Lee
(74) Attorney, Agent, or Firm — Cantor Colburn LLP

(57) ABSTRACT

A photoacid generator includes those of formula (I):

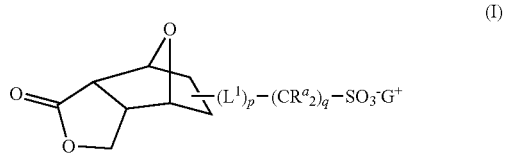

(I)

wherein each $R^a$ in formula 1 is independently H, F, a $C_{1-10}$ nonfluorinated organic group, $C_{1-10}$ fluorinated organic group, or a combination comprising at least one of the foregoing, provided at least one $R^a$ is F or a $C_{1-10}$ fluorinated organic group, the $C_{1-10}$ fluorinated and nonfluorinated organic groups each optionally comprising O, S, N, or a combination comprising at least one of the foregoing heteroatoms; $L^1$ is a linking group comprising a heteroatom comprising O, S, N, F, or a combination comprising at least one of the foregoing; $G^+$ is an onium salt of the formula (II):

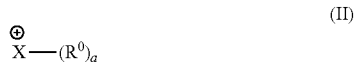

(II)

wherein in formula (II), X is S or I, each $R^0$ is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, provided at least one $R^0$ is substituted where each $R^0$ is a $C_6$ monocyclic aryl group, and wherein when X is I, a is 2, and where X is S, a is 3, p is 0 or 1, and q is an integer of from 1 to 10.

13 Claims, No Drawings

PHOTOACID GENERATOR AND PHOTORESIST COMPRISING SAME

CROSS REFERENCE TO RELATED APPLICATIONS

This application claims the benefit of U.S. Patent Application Ser. No. 61/582,341, filed Dec. 31, 2011, which is incorporated by reference herein in its entirety.

BACKGROUND

Improved photolithographic technologies based on short wavelength radiation (e.g., as generated by an ArF excimer laser operating at 193 nm), or other such short wavelength sources, are useful in the pursuit of ever faster and more efficient semiconductor devices by increasing device density of an integrated circuit. Photoresist materials useful in such short wavelength applications include chemical amplification-type radiation-sensitive resin compositions, which rely on the efficient interaction of a resin component having an acid labile functional group, and a photoacid generator (PAG) that generates an acid upon irradiation.

The requisite properties for photoresist materials useful for ArF excimer laser lithographies include transparency (i.e., low optical density) at 193 nm, as well as high etch resistance, conveyed by high carbon density and polycyclic ring structures. Useful photoresist platform resins include those based on a poly(meth)acrylate-based backbone and a carboxylic acid moiety protected with a bulky tertiary alkyl group, which is highly transparent at 193 nm. The efficiency of deprotecting (also referred to herein as "deblocking") the carboxylic acid directly correlates with the contrast and resolution.

PAG anions have increasingly been designed to be larger and bulkier in order to suppress acid diffusion during PEB for higher resolution. However, this trend often causes higher defectivity due to poor solubility of the bulky hydrophobic PAG in developer and in rinsing water. One way to simultaneously achieve low diffusivity and good defectivity level is to simultaneously increase both the size and the polarity character of the PAG anion by attaching large and hydrophilic moieties. By doing so, the size of the PAG anion can be sufficiently large enough to suppress acid diffusion at the time of PEB and the highly polar photoacid readily dissolves readily in basic developer (such as tetramethylammonium hydroxide, TMAH) which in turn leads to lower defect levels (i.e., lower defectivity).

STATEMENT OF INVENTION

The above and other problems of the prior art are overcome by a photoacid generator of formula (I):

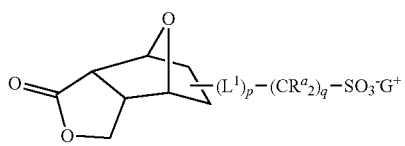

(I)

wherein each $R^a$ in formula (I) is independently H, F, a $C_{1-10}$ nonfluorinated organic group, $C_{1-10}$ fluorinated organic group, or a combination comprising at least one of the foregoing, provided at least one $R^a$ is F or a $C_{1-10}$ fluorinated organic group, the $C_{1-10}$ fluorinated and nonfluorinated organic groups each optionally comprising O, S, N, or a combination comprising at least one of the foregoing heteroatoms; $L^1$ is a linking group comprising a heteroatom comprising O, S, N, F, or a combination comprising at least one of the foregoing; $G^+$ is an onium salt of the formula (II):

(II)

wherein in formula (II), X is S or I, each $R^0$ is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, provided at least one $R^0$ is substituted where each $R^0$ is a $C_6$ monocyclic aryl group, and wherein when X is I, x is 2, and where X is S, x is 3, p is 0 or 1, and q is an integer of from 1 to 10.

A photoresist comprises the photoacid generator and an acid deprotectable copolymer.

A coated film comprises: (a) a substrate having one or more layers to be patterned on a surface thereof; and (b) a layer of the photoresist of claim 10 over the one or more layers to be patterned.

DETAILED DESCRIPTION OF THE INVENTION

Disclosed herein is a novel, highly polar compound for use as a photoacid generator, and based on a highly oxygenated tricyclic ring structure having a 5-membered lactone portion and a bridging oxygen atom, with a tethered tail portion terminating in a fluoroalkyl sulfonate group. The tricyclic ring structure is a 3-oxo-4,10-oxa-tricyclo[5,2,1,0$^{2,6}$]nonan group, in which the tail is attached either endo- or exo- to the lactone end, at either the 8- or 9-position on the ring. A variety of onium cations, including those based on sulfonium and iodonium cation centers, are useful to prepare the photoacid generator as a salt, where the photoacid generator is sensitive to actinic radiation below 300 nm, and in particular, to UV radiation of 248 nm or below. A photoresist comprising the photoacid generator has improved performance applications such as 193 nm immersion lithography, where the photoacid generator possesses structural and chemical properties for improving the photoacid diffusion rate, providing improved miscibility with other photoresist components, and reduced defect level after development.

A photoacid generator thus includes a compound of formula (I):

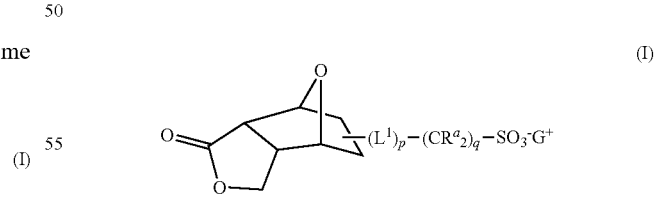

(I)

wherein each $R^a$ in formula (I) is substituted or unsubstituted and is independently H, F, a $C_{1-10}$ nonfluorinated organic group, $C_{1-10}$ fluorinated organic group, or a combination comprising at least one of the foregoing, provided at least one $R^a$ is F or a $C_{1-10}$ fluorinated organic group. The $C_{1-10}$ fluorinated and nonfluorinated organic groups may each optionally include O, S, N, or a combination comprising at least one of the foregoing heteroatoms, to introduce functionality to these groups.

As used throughout the specification and unless otherwise specified, "substituted" means having a substituent group including —OH, —SH, —CN, halogens including F, Cl, Br, or I, carboxylic acid, carboxylate, $C_{1-10}$ alkyl, $C_{3-10}$ cycloalkyl, $C_{6-10}$ aryl, $C_{7-10}$ aralkyl, $C_{1-10}$ alkyl, $C_{1-10}$ fluoroalkyl, $C_{3-10}$ fluorocycloalkyl, $C_{6-10}$ fluoroaryl, $C_{7-10}$ fluoroaralkyl, $C_{1-10}$ alkyl, $C_{1-10}$ alkoxy, $C_{3-10}$ cycloalkoxy, $C_{6-10}$ aryloxy, $C_{1-10}$ alkyl, a $C_{2-10}$ ester-containing group, a $C_{1-10}$ amide-containing group, a $C_{2-10}$ imide-containing group, a $C_{3-10}$ lactone-containing group, a $C_{3-10}$ lactam-containing group, a $C_{2-10}$ anhydride-containing group, or a combination comprising at least one of the foregoing.

Also in Formula (I), $L^1$ is a linking group comprising a heteroatom comprising O, S, N, F, or a combination comprising at least one of the foregoing. Preferably, $L^1$ is a $C_{1-30}$ linking group and where it is of C3 or greater, may be linear or branched. Also preferably, $L^1$ comprises functional groups such as an ether, ester, amine, amide, ketone, acetal, ketal, sulfide, disulfide, thiocarbonyl, sulfonate, sulfonamide, or a combination comprising at least one of the foregoing groups. The functional groups may be included in the connectivity of the pendant group, or may be a side chain, or both. More preferably, $L^1$ is linear or branched, and fluorinated or non-fluorinated, and comprises a $C_{1-10}$ alkylene, $C_{1-10}$ alkyleneoxy, $C_{1-10}$ ester, $C_{1-10}$ amide, $C_{1-10}$ sulfonate, $C_{1-10}$ sulfonamide, or a combination comprising at least one of the foregoing.

In addition, p is 0 or 1, and q is an integer of from 1 to 10.

Also in formula (I), $G^+$ is an onium salt of the formula:

(II)

wherein in formula (II), X is S or I, each $R^0$ is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, provided at least one $R^0$ is substituted where each $R^0$ is a $C_6$ monocyclic aryl group. Also in formula (II), where X is I, x is 2, and where X is S, x is 3.

Preferably, the photoacid generator has the formula (III):

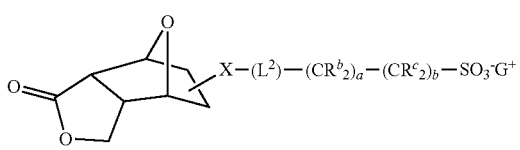

(III)

wherein X is N, O, or a single bond, $L^2$ is linear or branched, and fluorinated or non-fluorinated, and comprises a $C_{1-10}$ alkylene, $C_{1-10}$ alkyleneoxy, $C_{1-10}$ ester, $C_{1-10}$ amide, $C_{1-10}$ sulfonate, $C_{1-10}$ sulfonamide, or a combination comprising at least one of the foregoing. It will be understood that where X is O, an ester or sulfonate is obtained, whereas when X is N, an amide or sulfonamide is obtained.

Also in formula (III), $R^b$ is H, a linear or branched $C_{1-10}$ alkyl group, or a combination comprising at least one of the foregoing. Further, each $R^c$ is H, F, a $C_{1-10}$ fluorinated organic group, or a combination comprising at least one of the foregoing provided at least one $R^c$ is not H. In addition, a is an integer of 0 to 10, and b is an integer of from 1 to 10 provided that a+b is less than or equal to 10. $G^+$ is as defined in formula (II).

More preferably, the photoacid generator can have the formula (IV):

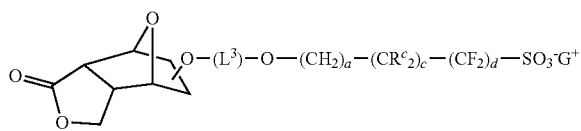

(IV)

wherein $L^3$ is a carbonyl, $C_{1-10}$ alkylene, $C_{1-10}$ alkyleneoxy, $C_{1-10}$ ester, or a combination comprising at least one of the foregoing, each $R^c$ is H, F, a $C_{1-10}$ fluorinated organic group, or a combination comprising at least one of the foregoing.

Also in formula (IV), a and c are each an integer of from 0 to 9, and d is an integer of from 1 to 10, provided a+c+d is less than or equal to 10, and $G^+$ is as defined for formula (II).

Useful photoacid generators include those having the formula (V):

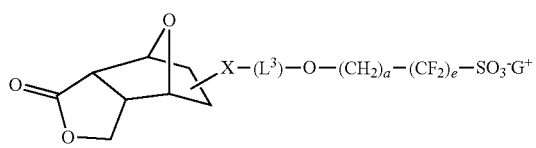

(V)

wherein $L^3$ is a carbonyl, $C_{1-10}$ alkylene, $C_{1-10}$ alkyleneoxy, $C_{1-10}$ ester, or a combination comprising at least one of the foregoing, a is an integer of from 0 to 9, and e is an integer of from 1 to 10, provided a+e is less than or equal to 10, and $G^+$ is as defined for formula (II).

Exemplary photoacid generators include those having the formulas:

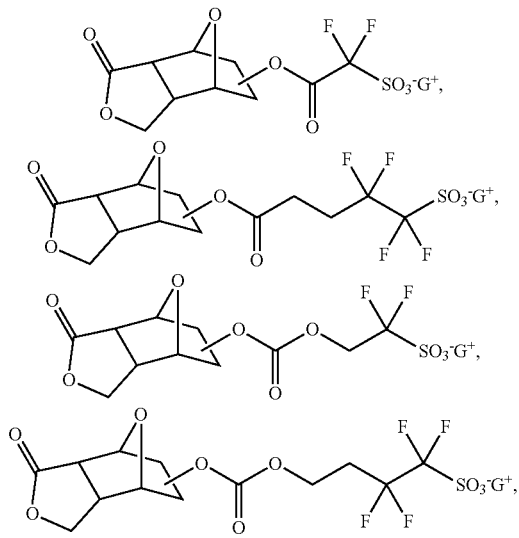

-continued

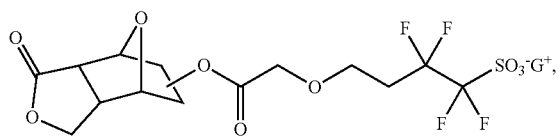

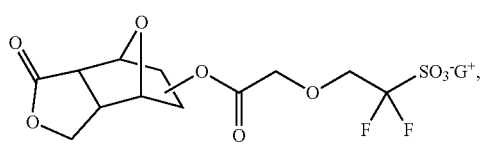

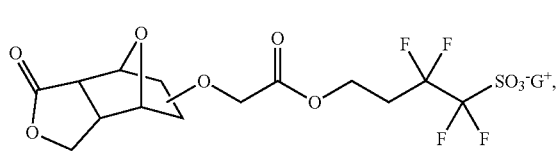

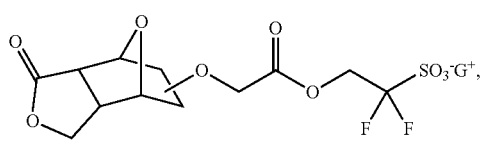

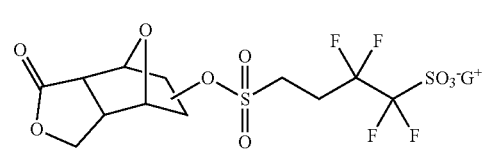

or

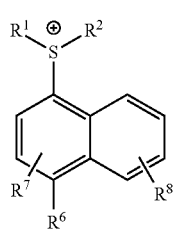

wherein $G^+$ is as defined for formula (II).

Also preferably, the onium salt $G^+$ of formula (II) is a sulfonium salt (where X is S in formula (II)) of the formulas (X) to (XV):

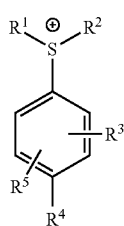
(X)

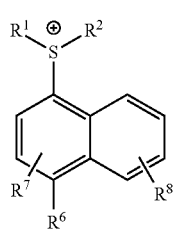
(XI)

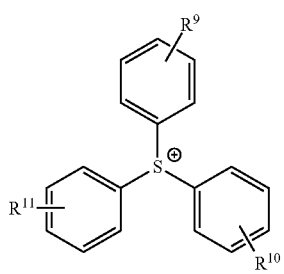
(XII)

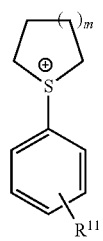
(XIII)

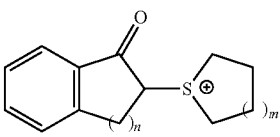
(XIV)

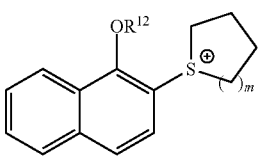
(XV)

wherein, in the above formulas (X) to (XV), $R^1$ and $R^2$ are independently H, a linear or branched $C_{1-10}$ alkyl group, $C_{2-10}$ alkenyl, $C_{1-10}$ fluoroalkyl group, $C_{7-10}$ aralkyl group, $C_{6-10}$ aryl group, or a combination comprising at least one of the foregoing, wherein $R^1$ and $R^2$ are separate or are connected via a single or double bond to form a carbocycle or heterocycle.

In addition, $R^3$, $R^4$, $R^5$, $R^6$, $R^7$, $R^8$, $R^9$, $R^{10}$, $R^{11}$, and $R^{12}$ are each independently H, halogen, $C_{1-10}$ alkyl, $C_{1-10}$ alkoxy, $C_{6-10}$ aryl, a thiophenoxy, a thioalkoxy, alkoxycarbonyl, or a combination comprising at least one of the foregoing, wherein $R^3$, $R^4$, $R^5$, $R^6$, $R^7$, $R^8$, $R^9$, $R^{10}$, $R^{11}$, and $R^{12}$ each optionally include an acid labile group, a base labile group or a base soluble group, and m is an integer of from 1 to 10, and n is 1 or 2.

Exemplary onium cations $G^+$ include those of the following formulas:

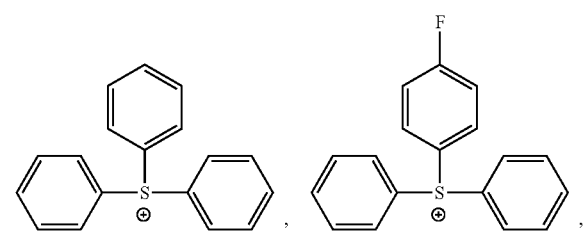
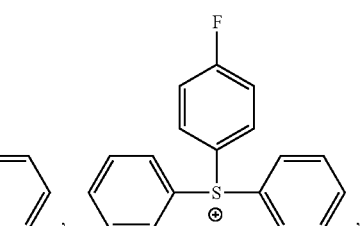
,

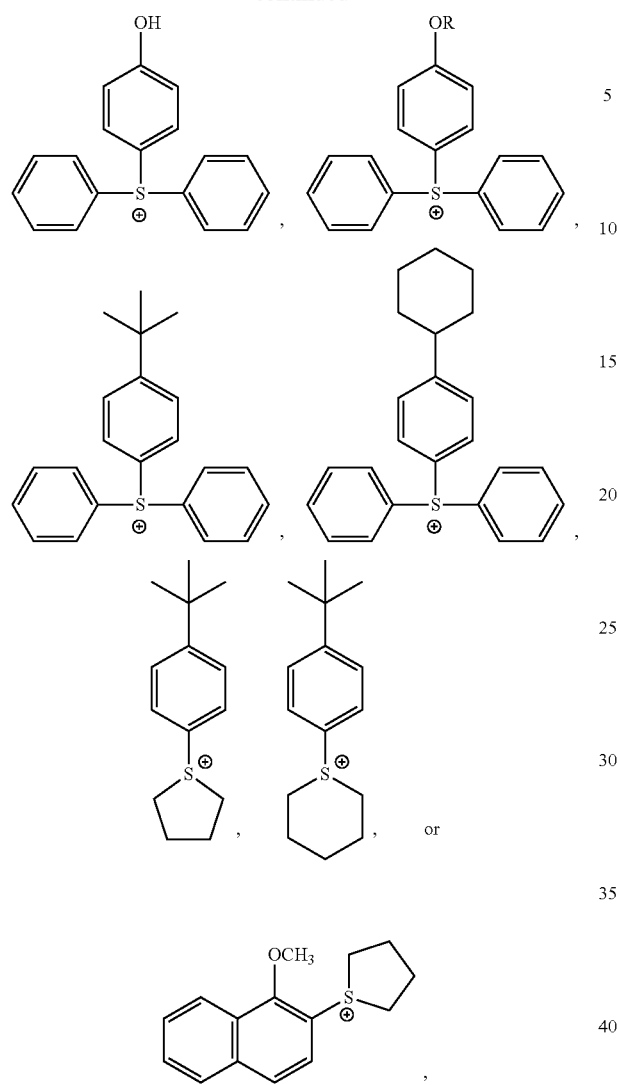

wherein R is a $C_{1-10}$ alkyl, $C_{1-10}$ fluoroalkyl, $C_{3-10}$ cycloalkyl, $C_{6-10}$ aryl, $C_{7-10}$ aralkyl, or a combination comprising at least one of the foregoing.

In addition, a photoresist comprising the photoacid generator of formula (I) and an acid deprotectable copolymer is disclosed.

The acid deprotectable copolymer includes, preferably, a (meth)acrylate monomer having a base soluble group, a (meth)acrylate monomer having a lactone functional group, a (meth)acrylate monomer having an acid-deprotectable group, or a combination comprising at least one of the foregoing monomers. As used herein, "(meth)acrylate" means acrylate or methacrylate or a combination comprising at least one of these polymerizable groups.

Other monomers, such as (meth)acrylate monomers for improving adhesion, etch resistance, etc., may also be included.

Any base-soluble monomer useful for forming an acid deprotectable copolymer for a 193 nm photoresist may be used. Exemplary base-soluble (meth)acrylate monomers may include, but are not limited to:

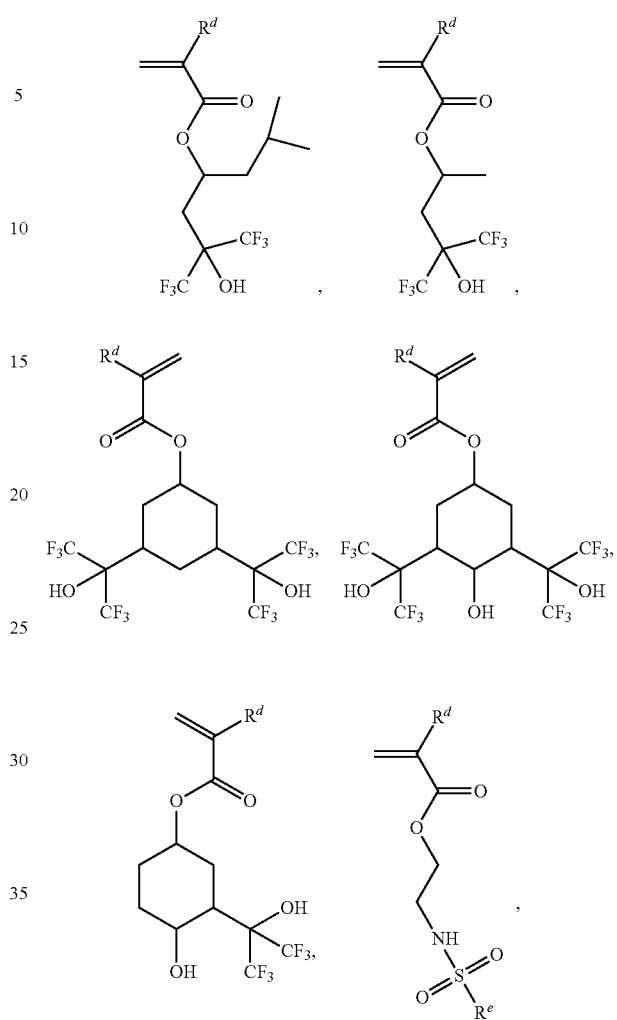

or a combination comprising at least one of the foregoing monomers, wherein $R^d$ is H, F, $C_{1-10}$ alkyl, or $C_{1-10}$ fluoroalkyl, and $R^e$ is a $C_{1-4}$ perfluoroalkyl group.

Any lactone-containing monomer useful for forming a 193 nm photoresist polymer may be used. Exemplary such lactone-containing monomers may include, but are not limited to:

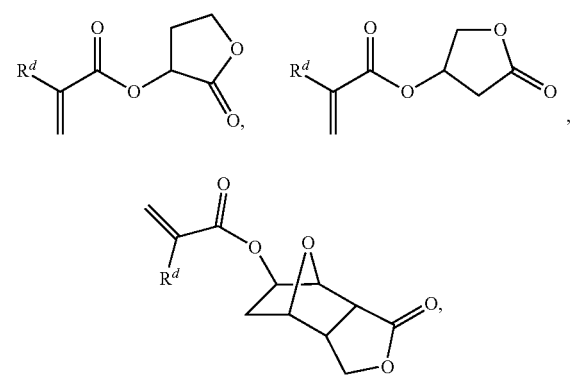

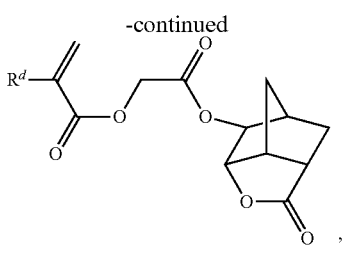

or a combination comprising at least one of the foregoing monomers, wherein $R^d$ is H, F, $C_{1-10}$ alkyl, or $C_{1-10}$ fluoroalkyl.

Any acid-deprotectable monomer useful for forming an acid deprotectable copolymer may also be used. Exemplary acid-deprotectable monomers may include, but are not limited to:

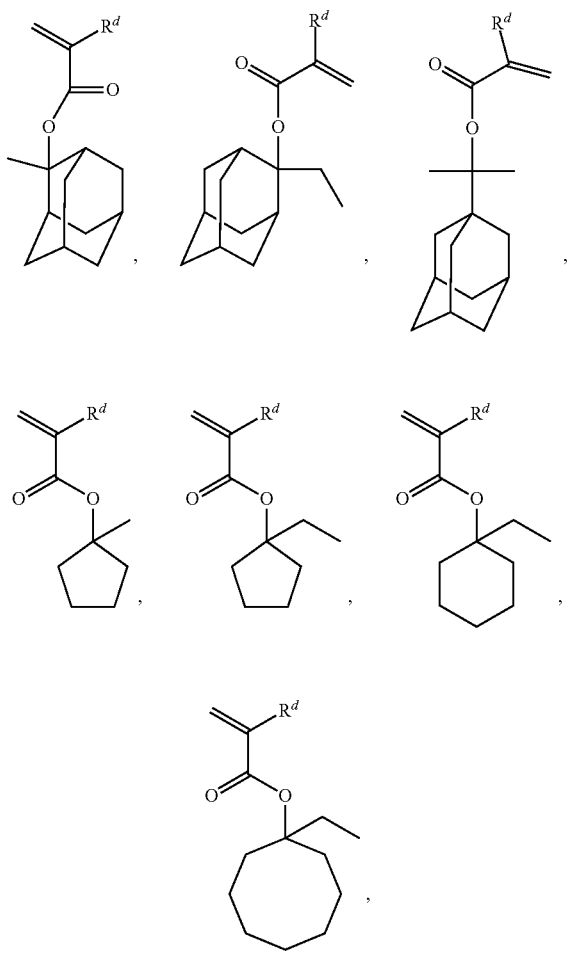

or a combination comprising at least one of the foregoing monomers, wherein $R^d$ is H, F, $C_{1-10}$ alkyl, or $C_{1-10}$ fluoroalkyl.

The copolymer may also include other monomers, including cage-structured monomers for enhancing etch resistance, with or without functional groups for improving adhesion. An exemplary additional monomer may include:

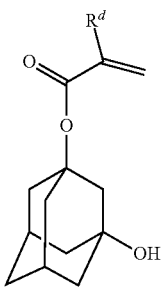

or a combination comprising the foregoing and at least one additional monomer, wherein $R^d$ is H, $C_{1-6}$ alkyl, or $CF_3$.

The photoresist optionally includes a second photoacid generator not identical to the photoacid generator of formula (I), and an amine or amide additive.

The second photoacid generator includes any such photoacid generator known or suitable for formulating photoresists for use at 193 nm.

The photoresist composition may further an amine or amide compound, referred to herein as a quencher. Quenchers may more broadly include, for example, those based on hydroxides, carboxylates, amines, imines, and amides. In an embodiment, a useful quencher is an amine, an amide, or a combination comprising at least one of the foregoing. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as Troger's base, a hindered amine such as diazabicycloundecene (DBU) or diazabicyclononene (DBN), N-protected amines such as N-t-butylcarbonyl-1,1-bis(hydroxymethyl)-2-hydroxyethylamine (TBOC-TRIS), or ionic quenchers including quaternary alkyl ammonium salts such as tetrabutylammonium hydroxide (TBAH) or tetrabutyl ammonium lactate.

Other components of the photoresist may include solvents and surfactants.

Solvents generally suitable for dissolving, dispensing, and coating the components include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist composition disclosed herein may include the copolymer in an amount of 50 to 99 wt %, specifically 55 to 95 wt %, more specifically 60 to 90 wt %, and still more specifically 65 to 90 based on the total weight of solids. It will be understood that "copolymer" used in this context of a component in a photoresist may mean one or more polymers useful in a photoresist. The photoacid generator may be present in the photoresist in an amount of 0.01 to 20 wt %, specifically 0.1 to 15 wt %, and still more specifically 0.2 to 10 wt %, based on the total weight of solids. A surfactant may be included in an amount of 0.01 to 5 wt %, specifically 0.1 to 4 wt %, and still more specifically 0.2 to 3 wt %, based on the total weight of solids. A quencher may be included in relatively small amounts of for example, from 0.03 to 5 wt % based on the total weight of solids. Other additives may be included in amounts of less than or equal to 30 wt %, specifically less than or equal to 20%, or more specifically less than or equal to 10%, based on the total weight of solids. The total solids content for the photoresist composition may be 0.5 to 50 wt %, specifically 1 to 45 wt %, more specifically 2 to 40 wt %, and still more specifically 5 to 35 wt %, based on the total weight of solids and solvent. It will be understood that the solids includes copolymer, photoacid generator, quencher, surfactant, and any optional additives, exclusive of solvent.

The photoresist disclosed herein may be used to form a film comprising the photoresist, where the film on the substrate constitutes a coated substrate. Such a coated substrate includes: (a) a substrate having one or more layers to be patterned on a surface thereof; and (b) a layer of the photoresist composition over the one or more layers to be patterned. Preferably, patterning is carried out using ultraviolet radiation at wavelength of less than 248 nm, and in particular, at 193 nm. In an embodiment, a patternable film comprises a photoacid generator of formula (I).

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 200 mm, 300 mm, or larger in diameter, or other dimensions useful for wafer fabrication production.

The invention includes at least the following embodiments.

Embodiment 1: A photoacid generator of formula (I):

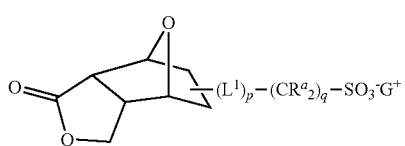

wherein each $R^a$ in formula 1 is independently H, F, a $C_{1-10}$ nonfluorinated organic group, $C_{1-10}$ fluorinated organic group, or a combination comprising at least one of the foregoing, provided at least one $R^a$ is F or a $C_{1-10}$ fluorinated organic group, the $C_{1-10}$ fluorinated and nonfluorinated organic groups each optionally comprising O, S, N, or a combination comprising at least one of the foregoing heteroatoms; $L^1$ is a linking group comprising a heteroatom comprising O, S, N, F, or a combination comprising at least one of the foregoing; $G^+$ is an onium salt of the formula (II):

wherein in formula (II), X is S or I, each $R^0$ is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, provided at least one $R^0$ is substituted where each $R^0$ is a $C_6$ monocyclic aryl group, and wherein when X is I, x is 2, and where X is S, x is 3, and p is 0 or 1, q is an integer of from 1 to 10.

Embodiment 2: The photoacid generator of embodiment 1, wherein $L^1$ is a $C_{1-30}$ linking group comprising an ether, ester, amine, amide, ketone, acetal, ketal, sulfide, disulfide, thiocarbonyl, sulfonate, sulfonamide, or a combination comprising at least one of the foregoing groups.

Embodiment 3: The photoacid generator of embodiment 1, wherein $L^1$ is linear or branched, and fluorinated or non-fluorinated, and comprises a $C_{1-10}$ alkylene, $C_{1-10}$ alkyleneoxy, $C_{1-10}$ ester, $C_{1-10}$ amide, $C_{1-10}$ sulfonate, $C_{1-10}$ sulfonamide, or a combination comprising at least one of the foregoing.

Embodiment 4: The photoacid generator of embodiment 1, having the formula

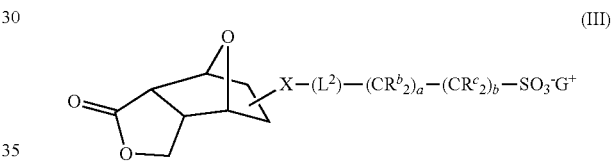

wherein X is N, O, or a single bond, $L^2$ is linear or branched, and fluorinated or non-fluorinated, and comprises a $C_{1-10}$ alkylene, $C_{1-10}$ alkyleneoxy, $C_{1-10}$ ester, $C_{1-10}$ amide, $C_{1-10}$ sulfonate, $C_{1-10}$ sulfonamide, or a combination comprising at least one of the foregoing, each $R^b$ is H, a linear or branched $C_{1-10}$ alkyl group, or a combination comprising at least one of the foregoing, each $R^c$ is H, F, a $C_{1-10}$ fluorinated organic group, or a combination comprising at least one of the foregoing provided at least one $R^c$ is not H, a is an integer of 0 to 10, and b is an integer of from 1 to 10 provided that a+b is less than or equal to 10, and G.

Embodiment 5: The photoacid generator of embodiment 1, having the formula (IV):

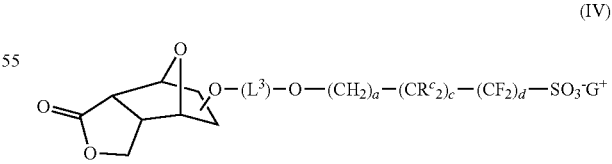

wherein $L^3$ is a carbonyl, $C_{1-10}$ alkylene, $C_{1-10}$ alkyleneoxy, $C_{1-10}$ ester, or a combination comprising at least one of the foregoing, each $R^c$ is H, F, a $C_{1-10}$ fluorinated organic group, or a combination comprising at least one of the foregoing, a and c are each an integer of from 0 to 9, and d is an integer of from 1 to 10, provided a+c+d is less than or equal to 10, and $G^+$ is as defined for Formula (II).

Embodiment 6: The photoacid generator of embodiment 1, having the formula (V):

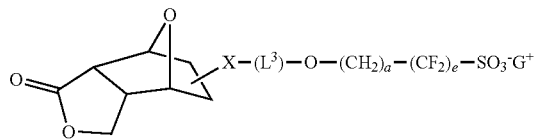
(V)

wherein $L^3$ is a carbonyl, $C_{1-10}$ alkylene, $C_{1-10}$ alkyleneoxy, $C_{1-10}$ ester, or a combination comprising at least one of the foregoing, a is an integer of from 0 to 9, and e is an integer of from 1 to 10, provided a+e is less than or equal to 10, and $G^+$ is as defined for Formula (II).

Embodiment 7: The photoacid generator of embodiment 1, having the formula:

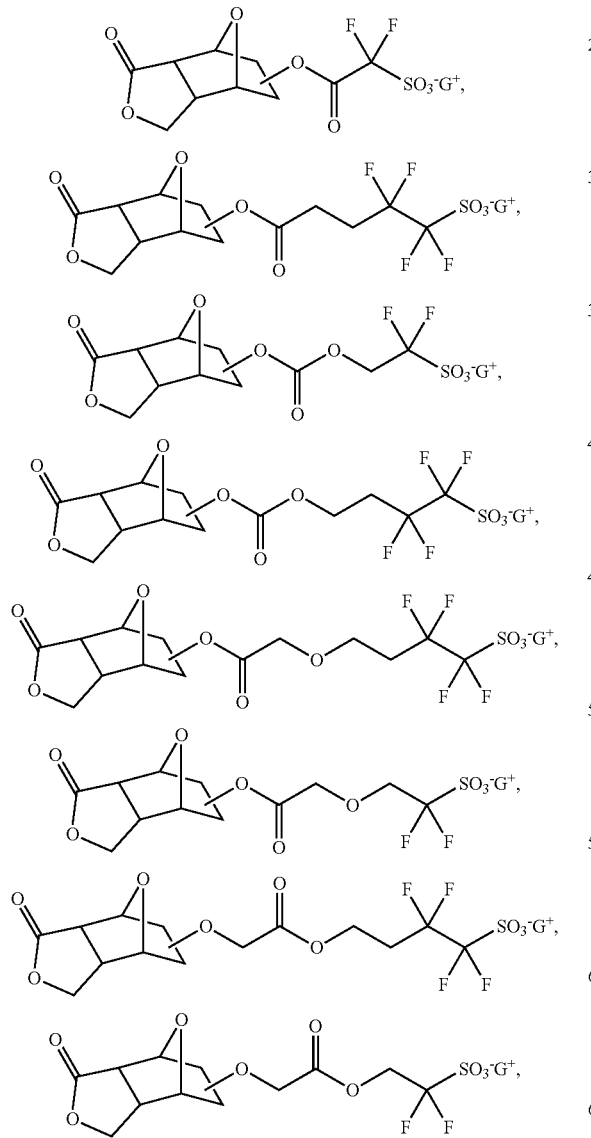

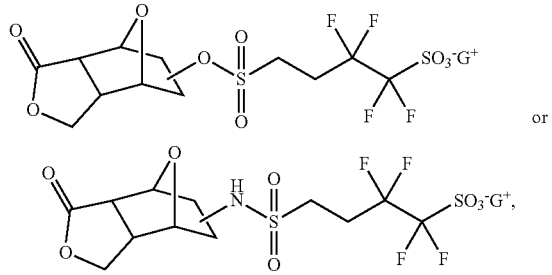

or wherein $G^+$ is as defined for Formula (II).

Embodiment 8: The photoacid generator of any of embodiments 1-7, wherein $G^+$ is sulfonium salt of the formula X to XV:

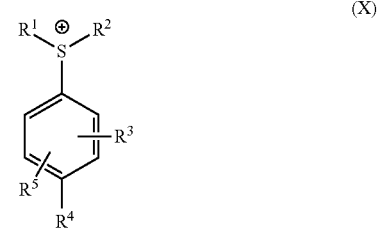
(X)

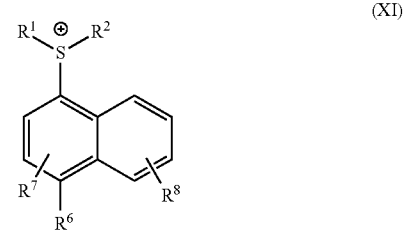
(XI)

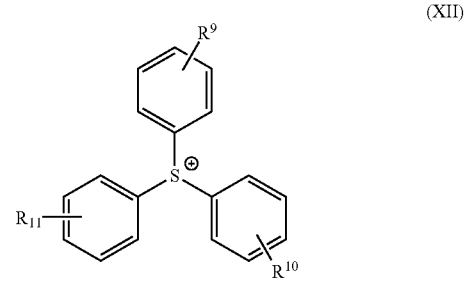
(XII)

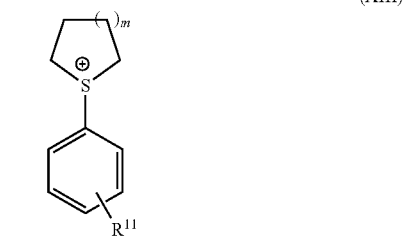
(XIII)

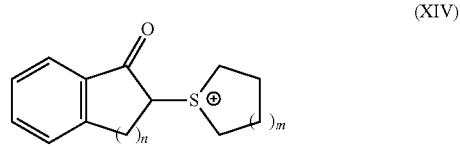
(XIV)

-continued

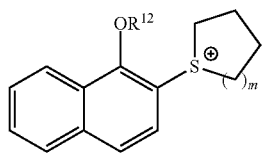

(XV)

-continued

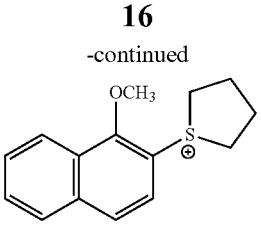

wherein $R^1$ and $R^2$ are independently H, a linear or branched $C_{1-10}$ alkyl group, $C_{2-10}$ alkenyl, $C_{1-10}$ fluoroalkyl group, $C_{7-10}$ aralkyl group, $C_{6-10}$ aryl group, or a combination comprising at least one of the foregoing, wherein $R^1$ and $R^2$ are separate or are connected via a single or double bond to form a carbocycle or heterocycle, $R^3$, $R^4$, $R^5$, $R^6$, $R^7$, $R^8$, $R^9$, $R^{10}$, $R^{11}$, and $R^{12}$ are each independently H, halogen, $C_{1-10}$ alkyl, $C_{1-10}$ alkoxy, $C_{6-10}$ aryl, a thiophenoxy, a thioalkoxy, alkoxycarbonyl, or a combination comprising at least one of the foregoing, wherein $R^3$, $R^4$, $R^5$, $R^6$, $R^7$, $R^8$, $R^9$, $R^{10}$, $R^{11}$, and $R^{12}$ each optionally include an acid labile group, a base labile group or a base soluble group, m is an integer of from 1 to 10, and n is 1 or 2.

Embodiment 9: The photoacid generator of any of embodiments 1-7, wherein $G^+$ has the formula:

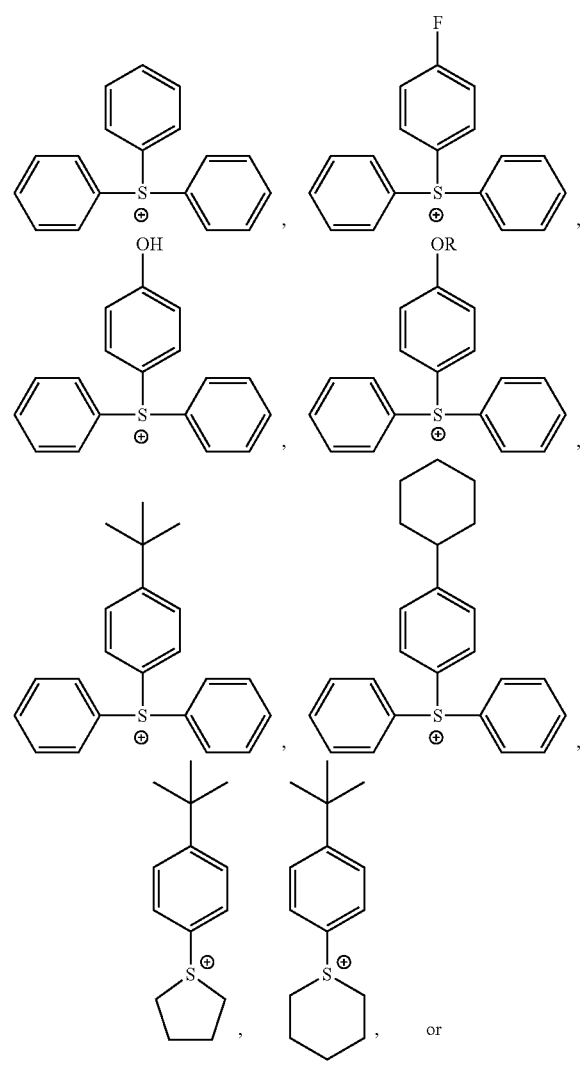

wherein R is a $C_{1-10}$ alkyl, $C_{1-10}$ fluoroalkyl, $C_{3-10}$ cycloalkyl, $C_{6-10}$ aryl, $C_{7-10}$ aralkyl, or a combination comprising at least one of the foregoing.

Embodiment 10: A photoresist comprising the photoacid generator of any of embodiments 1-9 and an acid deprotectable copolymer.

Embodiment 11: A coated film comprising: (a) a substrate having one or more layers to be patterned on a surface thereof; and (b) a layer of the photoresist of embodiment 10 over the one or more layers to be patterned.

The invention is further illustrated by the following examples. All compounds and reagents used herein are available commercially except where a procedure is provided below.

A mixture of two structural isomers 3-oxo-4,10-oxa-tricyclo[5,2,1,0$^{2,6}$]nonan-8-ol (compound A) and 3-oxo-4,10-oxa-tricyclo[5,2,1,0$^{2,6}$]nonan-9-ol (compound B) in 1:1 ratio was obtained commercially as 3-oxo-4,10-oxa-tricyclo[5,2,1,0$^{2,6}$]nonan-(8)9-ol and the structure is presented by formula C. Accordingly, all PAGs reported herein were obtained and used as a mixture of two structural isomers.

A

B

C

Triphenylsulfonium [3-oxo-4,10-oxa-tricyclo[5,2,1,0$^{2,6}$]nonan-(8)9-oxycarbonyl]-2,2-difluoroethanesulfonate (PAG 1) was synthesized in three steps as shown in Reaction Scheme 1 and as described below.

Reation Scheme 1

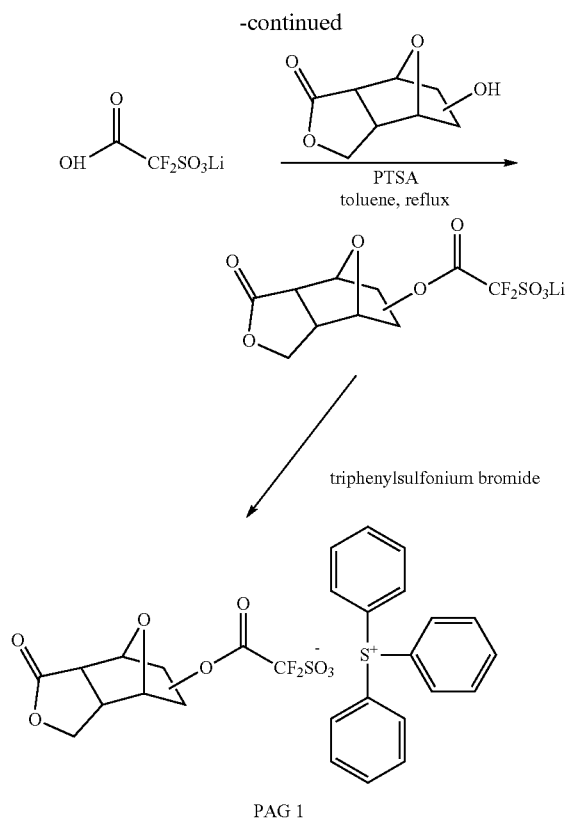

PAG 1

In the first step, methyl-2,2-difluoro-2-(fluorosulfonyl)acetate (56.6 g, 0.29 mol) was added dropwise to an aqueous solution of 23.1 g (0.96 mol) LiOH in 200 mL of water at 0° C. After completing the addition, the reaction mixture was warmed gradually to room temperature and then heated to reflux for 16 h. The mixture was cooled to room temperature and insoluble inorganic salts were removed by filtration. The filtrate was acidified by slow addition of 5N HCl to a pH of 1. Water was distilled off and the crude product was dried under reduced pressure to produce the product lithium difluorosulfoacetate as crude and white waxy solid.

In the second step, the crude lithium difluorosulfoacetate was mixed with 3-oxo-4,10-oxa-tricyclo[5,2,1,0$^{2,6}$]nonan-(8)9-ol (46.6 g, 0.273 mol) and p-toluenesulfonic acid monohydrate (104 g, 0.55 mol) in 600 mL of toluene. The mixture was heated at reflux with continuous removal of water (using a Dean-Stark trap). Reflux was continued for 2 days. The reaction mixture was cooled to room temperature and the solid was collected by filtration and dried. The isolated solid from this step was a mixture of raw materials, inorganic salts and the desired esterification product [3-oxo-4,10-oxa-tricyclo[5,2,1,0$^{2,6}$]nonan-(8)9-oxycarbonyl]-2,2-difluoroethanesulfonate lithium salt. $^{19}$F NMR of a sample of the solid indicated 47% conversion based on the parent alcohol.

In the third step, the crude 3-oxo-4,10-oxa-tricyclo[5,2,1,0$^{2,6}$]nonan-(8)$_9$-oxycarbonyl]-2,2-difluoroethanesulfonate lithium salt from the second step was mixed with triphenylsulfonium bromide (37.6 g, mmol) in 500 mL 1:1 mixture of dichloromethane/water. The mixture was stirred at room temperature for 16 h. The organic phase was separated, washed with water (5×200 mL) and the solvent was removed under reduced pressure. The resulting residue was dissolved in 100 mL acetone and poured slowly into 2 L of rapidly stirred methyl t-butyl ether. The solid was vacuum filtered, washed with methyl t-butyl ether, and dried in vacuo to produce triphenyl sulfonium [3-oxo-4,10-oxa-tricyclo[5,2,1,0$^{2,6}$]nonan-(8)9-oxycarbonyl]-2,2-difluoroethanesulfonate. (PAG 1).

Triphenylsulfonium [3-oxo-4,10-oxa-tricyclo[5,2,1,0$^{2,6}$]nonan-(8)9-oxycarbonyl]-3,3,4,4-tetrafluorobutane-4-sulfonate (PAG 2) was synthesized in four steps as shown in Reaction Scheme 2 and as described below.

Reaction Scheme 2

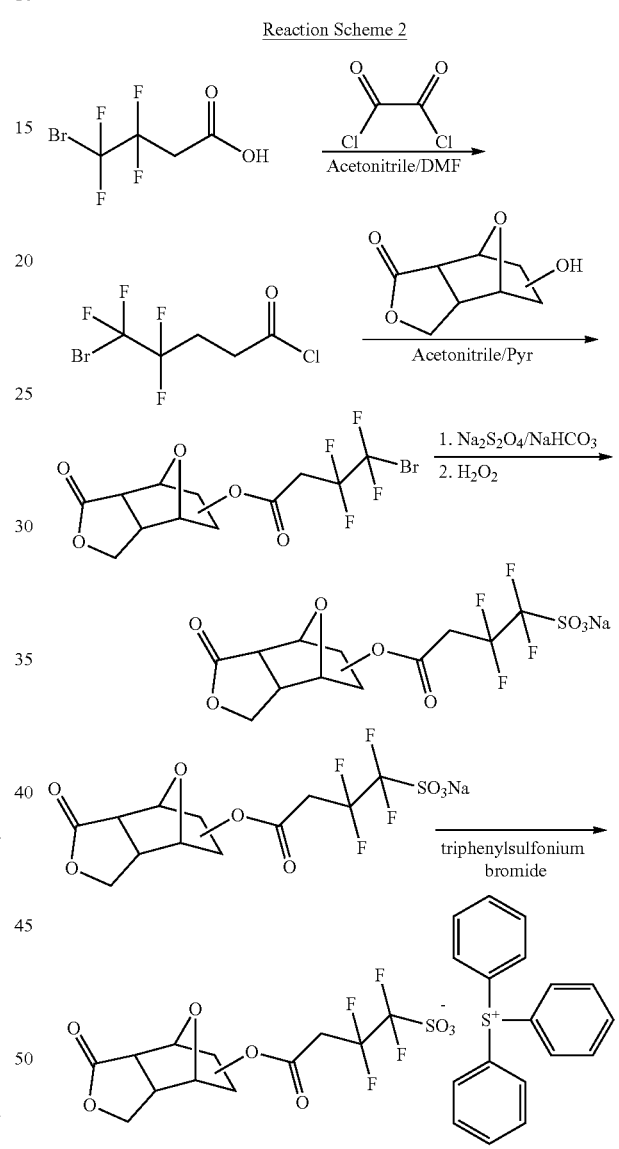

In the first step, the synthesis of 5-bromo-4,4,5,5-tetrafluoropentanoyl chloride was carried out as follows. In a 500 mL round bottom flask, 30 g (125.5 mmol) of 4-bromo-3,3,4,4-tetrafluorobutanoic acid was dissolved in 100 mL acetonitrile and 1 mL of N,N-dimethylformamide. Oxalyl chloride (16.0 g, 126.0 mmol) was added dropwise and the reaction mixture was stirred at room temperature for 2 h. The formation of 5-bromo-4,4,5,5-tetrafluoropentanoyl chloride intermediate product was confirmed by $^1$H NMR. The product in acetonitrile solution was used in the next step.

In the second step, a solution of 3-oxo-4,10-oxa-tricyclo[5,2,1,0$^{2,6}$]nonan-(8)9-ol (21.3 g, 125.0 mmol) in 200 mL acetonitrile was added to the 5-bromo-4,4,5,5-tetrafluoropentanoyl chloride solution. To the mixture was added 9.93 g (125.5 mmol) pyridine and the reaction was stirred at ambient temperature under nitrogen for 16 h. The solvent was removed under reduced pressure and the resulting oily residue was dissolved in 250 mL dichloromethane. The later solution was washed once with 200 mL 1 N HCl, washed once with 200 mL saturated aqueous NaHCO$_3$, dried over MgSO$_4$ and the solvent removed under reduced pressure to produce 3-oxo-4,10-oxa-tricyclo[5,2,1,0$^{2,6}$]nonan-(8)9-oxycarbonyl]-4-bromo-3,3,4,4-tetrafluorobutane as a white solid.

In the third step, 3-oxo-4,10-oxa-tricyclo[5,2,1,0$^{2,6}$]nonan-(8)9-oxycarbonyl]-4-bromo-3,3,4,4-tetrafluorobutane (40 g, 100 mmol) was dissolved in 350 mL acetonitrile. Sodium dithionite (35.6 g, 200 mmol) and sodium bicarbonate (17.2 g, 200 mmol) were dissolved in 350 mL deionized water. The aqueous solution was added to the stirred acetonitrile solution and the reaction mixture was stirred at 60° C. for 16 h. Reaction monitoring by $^{19}$F NMR indicated complete conversion. The aqueous phase saturated with NaCl and the phases were separated. The acetonitrile solution of the product 3-oxo-4,10-oxa-tricyclo[5,2,1,0$^{2,6}$]nonan-(8)$_9$-oxycarbonyl]-3,3,4,4-tetrafluorobutane-4-sulfonate was used in the next step.

In the fourth step, to the stirred acetonitrile solution from the third step was added 100 mL water, Na$_2$WO$_4$.2H$_2$O (100 mg) followed by H$_2$O$_2$ (30 w/w % aqueous, 20.8 g). The reaction was stirred at ambient temperature for 48 h. The reaction was cooled on an ice bath, stirred, and sodium bisulfite (10.18 g, 97.8 mmol) was added. After 10 minutes the ice bath was removed, the reaction saturated with NaCl, and stirred rapidly for 1 h. to homogenize. The phases were separated and the aqueous phase extracted with 250 mL acetonitrile. The combined organic phases were evaporated on the rotary evaporator. The residual solid was dissolved in 100 ml of acetone, and the solution was poured slowly into methyl t-butyl ether (2 liter). A waxy product obtained which was isolated by removing the solvents by decanting. The waxy product was further dried under reduced pressure. The overall yield for the crude product 3-oxo-4,10-oxa-tricyclo[5,2,1,0$^{2,6}$]nonan-(8)9-oxycarbonyl]-3,3,4,4-tetrafluorobutane-4-sulfonate sodium salt from the third and fourth step was 27.6 g (73%). The product was used in the next step without further purification.

In the fifth step, to a stirred mixture of 200 mL dichloromethane and 200 mL deionized water was added 3-oxo-4,10-oxa-tricyclo[5,2,1,0$^{2,6}$]nonan-(8)9-oxycarbonyl]-3,3,4,4-tetrafluorobutane-4-sulfonate sodium salt (25 g, 60.34 mmol) and triphenylsulfonium bromide (20 g, 58.26 mmol). The reaction was stirred at ambient temperature overnight. The phases were separated. The organic phase was washed five times with 250 mL volumes of deionized water. The organic phase was separated and the solution was concentrated by distilling off about 75% of the solvent. The resulting concentrated solution was poured slowly into 2 L stirred methyl t-butyl ether (MTBE) to produce the product as white crystalline solids. The solid was vacuum filtered, washed with MTBE, and dried under vacuum. This gave 33.0 g (86.5%) of the PAG triphenylsulfonium [3-oxo-4,10-oxa-tricyclo[5,2,1,0$^{2,6}$]nonan-(8)9-oxycarbonyl]-3,3,4,4-tetrafluorobutane-4-sulfonate (PAG 2) as a white solid.

T-butylphenyl diphenylsulfonium [3-oxo-4,10-oxa-tricyclo[5,2,1,0$^{2,6}$]nonan-(8)$_9$-oxycarbonyl]-3,3,4,4-tetrafluorobutane-4-sulfonate (PAG 3) was synthesized as follow. To a stirred mixture of 200 mL dichloromethane and 200 mL deionized water was added 25 g (60.34 mmol) 3-oxo-4,10-oxa-tricyclo[5,2,1,0$^{2,6}$]nonan-(8)9-oxycarbonyl]-3,3,4,4-tetrafluorobutane-4-sulfonate sodium salt (synthesized as described in example 2) and t-butylphenyl diphenylsulfonium bromide (23 g, 57.58 mmol). The reaction was stirred at ambient temperature overnight. The phases were separated. The organic phase was washed five times with 250 mL of deionized water. The organic phase was separated and the solution was concentrated by distilling off about 75% of the solvent. The resulting concentrated solution was poured slowly into 2 L stirred methyl t-butyl ether (MTBE) to produce the product as white crystalline solid. The solid was vacuum filtered, washed with MTBE, and dried under vacuum, to afford 28.0 g (65%) of the PAG t-butylphenyl diphenylsulfonium [3-oxo-4,10-oxa-tricyclo[5,2,1,0$^{2,6}$]nonan-(8)9-oxycarbonyl]-3,3,4,4-tetrafluorobutane-4-sulfonate (PAG 3) as a white solid.

A photoresist polymer (Polymer A1) for use in the lithographic evaluations (below) was prepared using monomers M1-M5 below, according to the following procedure.

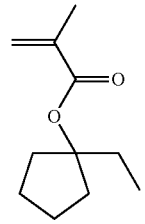

M1

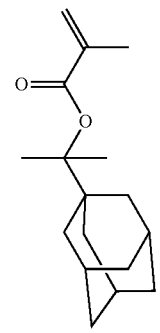

M2

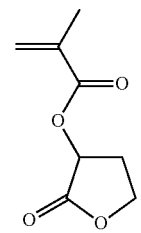

M3

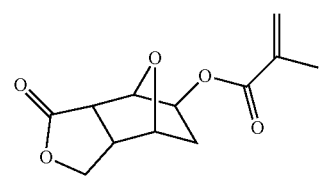

M4

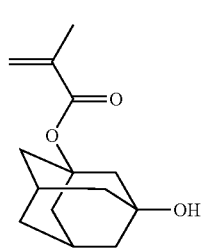

M5

A solution of 1-ethylcyclopentyl methacrylate (ECPMA, M1; 20 mmol), 1-isopropyl-adamantanyl methacrylate (IAM, M2; 20 mmol), 2-oxo-tetrahydro-furan-3-yl methacrylate (α-GBLMA, M3; 30 mmol), 3-oxo-4,10-dioxa-tricyclo[5.2.1.02,6]dec-8(or 9)-yl methacrylate (ODOTMA, M4; 20 mmol), and 3-hydroxy-adamantanyl methacrylate (HAMA, M5; 10 mmol) dissolved in 30 g of tetrahydrofuran (THF) was degassed by bubbling with nitrogen and charged to a 500 ml flask equipped with a condenser, nitrogen inlet and mechanical stirrer along with an additional 10 g of degassed THF. The solution is brought to reflux, and 6 g of dimethyl-2,2-azodiisobutyrate is dissolved in 5 g of THF and charged in to the flask. The polymerization mixture is then stirred for about 4 hours at reflux, after which time the reaction is diluted with 5 g of THF and the polymerization mixture cooled to room temperature. The polymer is precipitated by addition to 1.0 L of isopropanol, the solid collected by filtration, re-precipitated by dissolving in 50 g THF and dropwise addition to another 1.0 L isopropanol, and the precipitated polymer collected and dried under vacuum at 45° C. for 48 h. to yield photoresist polymer poly(IAM/ECPMA/α-GBLMA/ODOTMA/HAMA) (20:20:30:20:10 ratio, respectively). Mw=8,000.

The exemplary photoacid generator compounds PAG1, PAG2 and PAG3 were evaluated lithographically. The photoresists were formulated using the components and proportions shown in Table 1, below, to provide a photoresists and a comparative photoresist. Note that for each photoresist, the PAG (see table), base (t-butyloxycarbonyl-4-hydroxypyridine, TBOC-4HP), and surface leveling agent (SLA; also referred to as surfactant; PF 656, available from Omnova), are shown as a weight percentage based on the total solids content of the photoresist, with the balance of the solids being the polymer. The photoresists are further formulated using as solvents propylene glycol methyl ether acetate (S1) and methyl 2-hydroxyisobutyrate (S2) in a 1:1 ratio by weight. The photoresists and comparative photoresist were each diluted to a final solids of 4 wt %.

TABLE 1

| Example | Polymer (wt %) | PAG | PAG (wt %) | Base (wt %) | SLA (wt %) |
|---|---|---|---|---|---|
| CEx. 1 | 89.29 | Triphenylsulfonium perfluorobutane sulfonate | 9.58 | 1.03 | 0.10 |
| Ex. 1 | 88.804 | PAG1 | 10.06 | 1.029 | 0.10 |
| Ex. 2 | 87.474 | PAG2 | 11.397 | 1.029 | 0.10 |
| Ex. 3 | 86.517 | PAG3 | 12.354 | 1.029 | 0.10 |

Photoresists from Example 1, 2, 3 and Comparative Example 1 were lithographically processed as follows. The photoresist was spin coated onto a 200 mm silicon wafer having an organic antireflective coating (ARTM77, Rohm and Haas Electronic Materials LLC, baked at) and baked at 110° C. for 60 seconds, to form a resist film 100 nm in thickness. The photoresist was exposed with ArF excimer laser radiation (193 nm) using an ASML/1100 exposure tool (manufactured by ASML) with a numerical aperture (NA) of 0.75, under annular illumination with outer/inner sigma of 0.89/0.64 and focus offset/step 0.10/0.05. A line-space pattern mask targeting a linewidth of 90 nm and a pitch of 180 nm was used to image the features.

The patterned resist was post exposure baked (PEB) at 100° C. for 60 seconds followed by development with 0.26N aqueous tetramethylammonium hydroxide (TMAH) solution and subsequent water wash. For each example, an L/S pattern having a line width of 90 nm and a pitch of 180 nm was formed. Mask Error Factor (MEF) and Exposure Latitude (EL) were determined by top-down scanning electron microscopy (SEM) using images captured with a Hitachi 9380 CD-SEM, operating at an accelerating voltage of 800 volts (V), a probe current of 8.0 picoamperes (pA), and 200 Kx magnification. Exposure latitude (EL) was defined as a difference in exposure energy to print +/−10% of the target diameter normalized by the sizing energy. Mask Error Factor (MEF) was defined as the ratio of critical dimension (CD) change for the resolved photoresist pattern to the relative dimension change on the mask pattern.

Results from lithographic evaluation of formulations from Comparative Example 1 and Examples 1, 2 and 3 are shown in Table 2.

TABLE 2

| Example | $E_{size}$ (mJ/cm$^2$) | MEF | EL @ 10% of CD Target |
|---|---|---|---|
| CEx. 1 | 16.6 | 4.06 | 10.1 |
| Ex. 1 | 46.2 | 3.41 | 12.6 |
| Ex. 2 | 34.4 | 3.23 | 12.6 |
| Ex. 3 | 45.3 | 3.17 | 12.8 |

As seen in Table 2, the photoresist formulations (Ex. 1, Ex. 2 and Ex. 3) prepared using the exemplary PAGs above each show a higher exposure latitude and lower MEF values when compared with the nearly identical comparative photoresist formulation but prepared using the commercially available PAG triphenylsulfonium perfluorobutane sulfonate (CEx. 1). Thus, Ex.1, Ex.2 and Ex.3 which include exemplary PAGs according to the instant invention each show improved lithographic performance based on greater exposure latitude (EL) and lower mask error factor (MEF).

All ranges disclosed herein are inclusive of the endpoints, and the endpoints are independently combinable with each other. The suffix "(s)" as used herein is intended to include both the singular and the plural of the term that it modifies, thereby including at least one of that term. "Optional" or "optionally" means that the subsequently described event or circumstance can or cannot occur, and that the description includes instances where the event occurs and instances where it does not. As used herein, "combination" is inclusive of blends, mixtures, alloys, or reaction products. All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another.

The invention claimed is:
1. A mixture of structural isomers of a photoacid generator of formula (I):

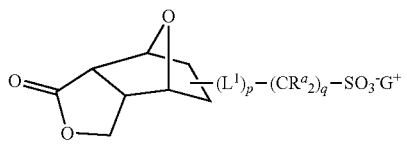

wherein
each $R^a$ in formula 1 is independently H, F, a $C_{1-10}$ nonfluorinated organic group, $C_{1-10}$ fluorinated organic group, or a combination comprising at least one of the foregoing, provided at least one $R^a$ is F or a $C_{1-10}$ fluorinated organic group, the $C_{1-10}$ fluorinated and nonfluorinated organic groups each optionally comprising O, S, N, or a combination comprising at least one of the foregoing heteroatoms;
$L^1$ is a linking group comprising a heteroatom comprising O, S, N, F, or a combination comprising at least one of the foregoing;
$G^+$ is an onium salt of the formula (II):

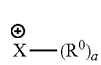

wherein in formula (II),
X is S or I,
each $R^0$ is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, provided at least one $R^0$ is substituted where each $R^0$ is a $C_6$ monocyclic aryl group, and wherein when X is I, x is 2, and where X is S, x is 3, and
p is 0 or 1, q is an integer of from 1 to 10.

2. The mixture of structural isomers of a photoacid generator of claim 1, wherein $L^1$ is a $C_{1-30}$ linking group comprising an ether, ester, amine, amide, ketone, acetal, ketal, sulfide, disulfide, thiocarbonyl, sulfonate, sulfonamide, or a combination comprising at least one of the foregoing groups.

3. The mixture of structural isomers of a photoacid generator of claim 1, wherein $L^1$ is linear or branched, and fluorinated or non-fluorinated, and comprises a $C_{1-10}$ alkylene, $C_{1-10}$ alkyleneoxy, $C_{1-10}$ ester, $C_{1-10}$ amide, $C_{1-10}$ sulfonate, $C_{1-10}$ sulfonamide, or a combination comprising at least one of the foregoing.

4. The mixture of structural isomers of a photoacid generator of claim 1, having the formula (III):

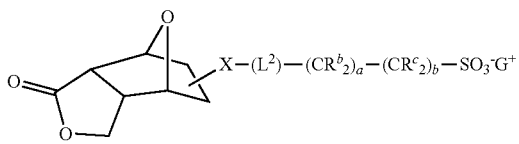

wherein X is N, O, or a single bond, $L^2$ is linear or branched, and fluorinated or non-fluorinated, and comprises a $C_{1-10}$ alkylene, $C_{1-10}$ alkyleneoxy, $C_{1-10}$ ester, $C_{1-10}$ amide, $C_{1-10}$ sulfonate, $C_{1-10}$ sulfonamide, or a combination comprising at least one of the foregoing, each $R^b$ is H, a linear or branched $C_{1-10}$ alkyl group, or a combination comprising at least one of the foregoing, each $R^c$ is H, F, a $C_{1-10}$ fluorinated organic group, or a combination comprising at least one of the foregoing provided at least one $R^c$ is not H, a is an integer of 0 to 10, and b is an integer of from 1 to 10 provided that a+b is less than or equal to 10, and $G^+$ is as defined in Formula (II).

5. The mixture of structural isomers of a photoacid generator of claim 1, having the formula (IV):

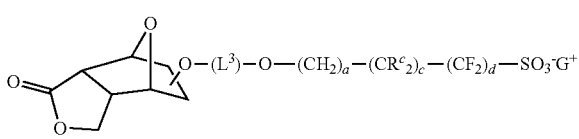

wherein $L^3$ is a carbonyl, $C_{1-10}$ alkylene, $C_{1-10}$ alkyleneoxy, $C_{1-10}$ ester, or a combination comprising at least one of the foregoing, each $R^c$ is H, F, a $C_{1-10}$ fluorinated organic group, or a combination comprising at least one of the foregoing, a and c are each an integer of from 0 to 9, and d is an integer of from 1 to 10, provided a+c+d is less than or equal to 10, and $G^+$ is as defined for Formula (II).

6. The mixture of structural isomers of a photoacid generator of claim 1, having the formula (V):

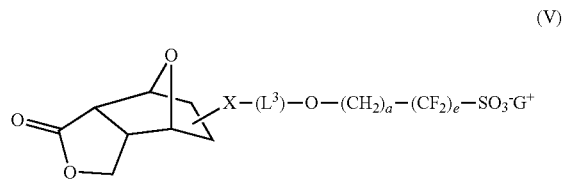

wherein $L^3$ is a carbonyl, $C_{1-10}$ alkylene, $C_{1-10}$ alkyleneoxy, $C_{1-10}$ ester, or a combination comprising at least one of the foregoing, a is an integer of from 0 to 9, and e is an integer of from 1 to 10, provided a+e is less than or equal to 10, and $G^+$ is as defined for Formula (II).

7. The mixture of structural isomers of a photoacid generator of claim 1, having the formula:

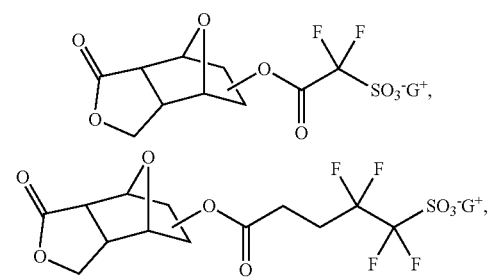

25

-continued

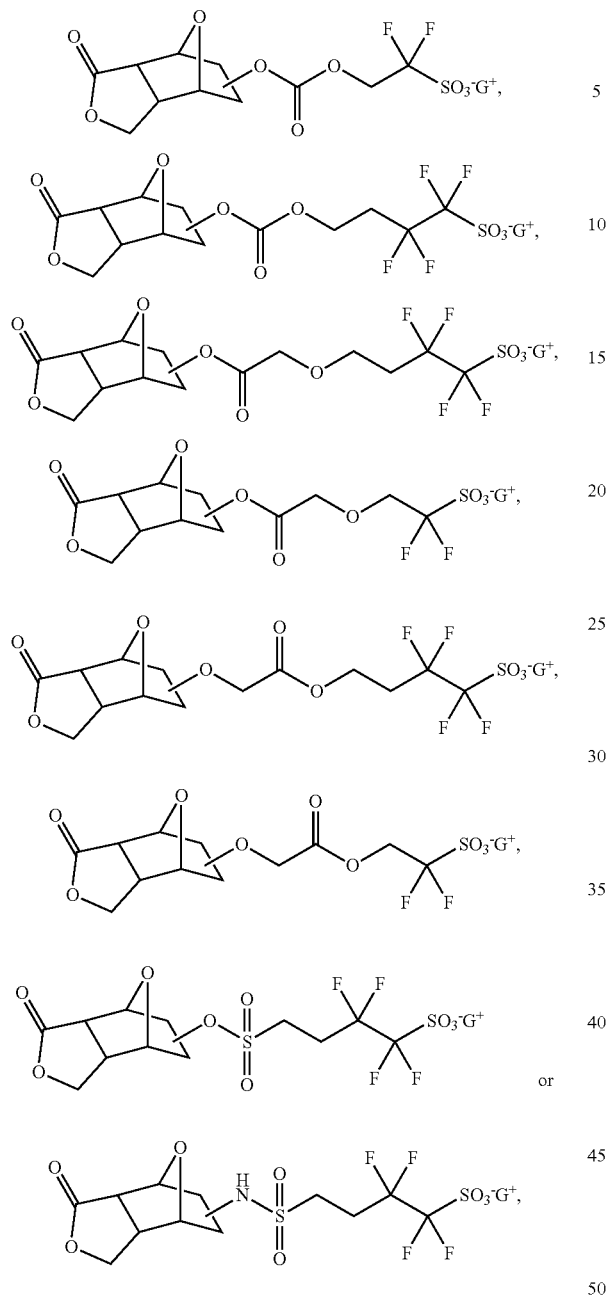

wherein G⁺ is as defined for Formula (II).

8. The mixture of structural isomers of a photoacid generator of claim 1, wherein G⁺ is sulfonium salt of the formula X to XV:

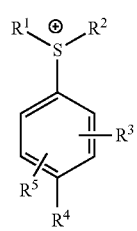
(X)

26

-continued

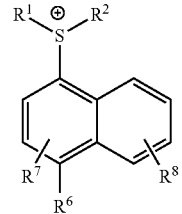
(XI)

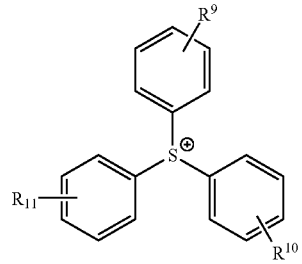
(XII)

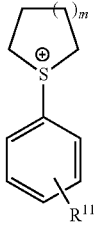
(XIII)

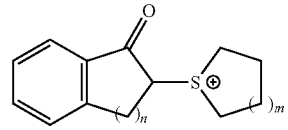
(XIV)

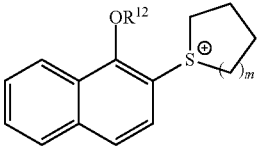
(XV)

wherein $R^1$ and $R^2$ are independently H, a linear or branched $C_{1-10}$ alkyl group, $C_{2-10}$ alkenyl, $C_{1-10}$ fluoroalkyl group, $C_{7-10}$ aralkyl group, $C_{6-10}$ aryl group, or a combination comprising at least one of the foregoing, wherein $R^1$ and $R^2$ are separate or are connected via a single or double bond to form a carbocycle or heterocycle, $R^3$, $R^4$, $R^5$, $R^6$, $R^7$, $R^8$, $R^9$, $R^{10}$, $R^{11}$, and $R^{12}$ are each independently H, halogen, $C_{1-10}$ alkyl, $C_{1-10}$ alkoxy, $C_{6-10}$ aryl, a thiophenoxy, a thioalkoxy, alkoxycarbonyl, or a combination comprising at least one of the foregoing, wherein $R^3$, $R^4$, $R^5$, $R^6$, $R^7$, $R^8$, $R^9$, $R^{10}$, $R^{11}$, and $R^{12}$ each optionally include an acid labile group, a base labile group or a base soluble group, m is an integer of from 1 to 10, and n is 1 or 2.

9. The mixture of structural isomers of a photoacid generator of claim 1, wherein G⁺ has the formula:

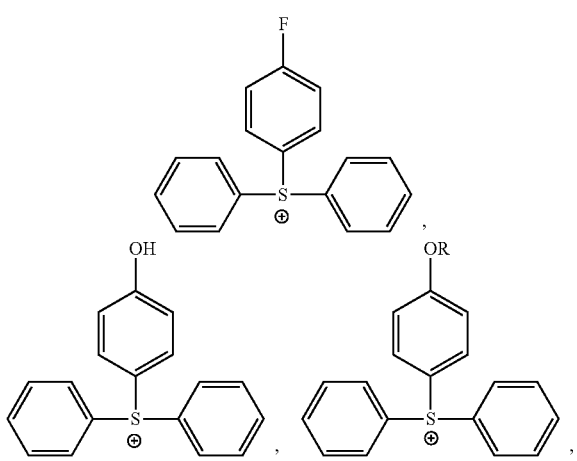

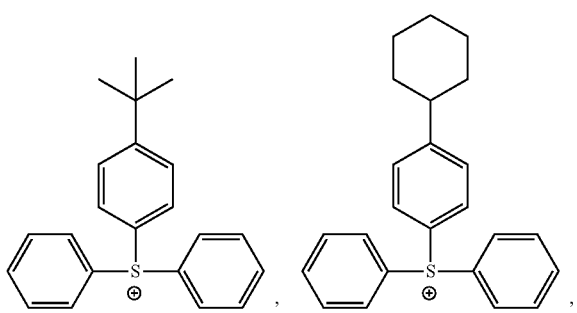

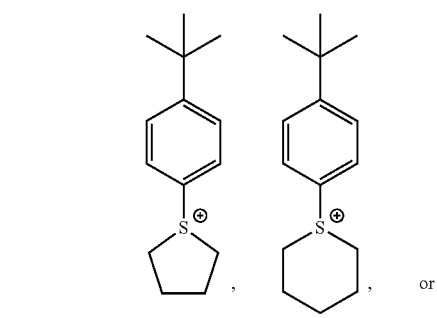

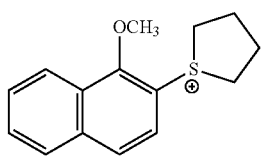

wherein R is a $C_{1-10}$ alkyl, $C_{1-10}$ fluoroalkyl, $C_{3-10}$ cycloalkyl, $C_{6-10}$ aryl, $C_{7-10}$ aralkyl, or a combination comprising at least one of the foregoing.

10. A photoresist comprising the mixture of structural isomers of a the photoacid generator of claim 1 and an acid deprotectable copolymer.

11. A coated film comprising: (a) a substrate having one or more layers to be patterned on a surface thereof; and (b) a layer of the photoresist of claim 10 over the one or more layers to be patterned.

12. A photoacid generator having the formula (III):

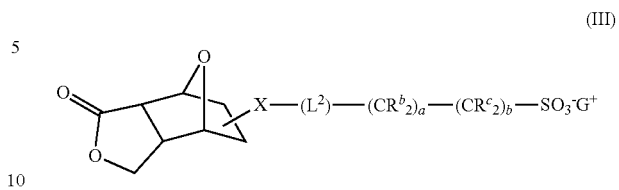

(III)

wherein in formula (III),

X in N, $L^2$ is linear or branched, and fluorinated or non-fluorinated, and comprises a $C_{1-10}$ alkylene, $C_{1-10}$ alkyleneoxy, $C_{1-10}$ amide, $C_{1-10}$ sulfonate, $C_{1-10}$ sulfonamide, or a combination comprising at least one of the foregoing, each $R^b$ is H, a linear or branched $C_{1-10}$ alkyl group, or a combination comprising at least one of the foregoing, each $R^c$ is H, F, a $C_{1-10}$ fluorinated organic group, or a combination comprising at least one of the foregoing provided at least one $R^c$ is not H, a is an integer of 0 to 10, and b is an integer of from 1 to 10 provided that a+b is less than or equal to 10, and $G^+$ is an onium salt of the formula (II):

(II)

wherein in formula (II),

X' is S or I, each $R^0$ is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, provided at least one $R^0$ is substituted where each $R^0$ is a $C_6$ monocyclic aryl group, and wherein when X' is I, x is 2, and when X' is S, x is 3.

13. A photoacid generator having the formula (IV):

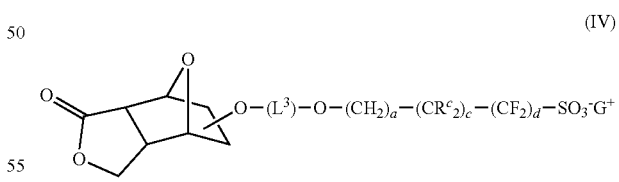

(IV)

wherein in formula (IV), $L^3$ is a carbonyl, $C_{1-10}$ alkylene, $C_{1-10}$ alkyleneoxy, $C_{1-10}$ ester, or a combination comprising at least one of the foregoing, each $R^c$ is H, F, a $C_{1-10}$ fluorinated organic group, or a combination comprising at least one of the foregoing, a and c are each an integer of from 0 to 9, and d is an integer of from 1 to 10, provided a+c+d is less than or equal to 10, and $G^+$ is an onium salt of the formula (II):

(II)

wherein in formula (II),
X is S or I,
each $R^o$ is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, provided at least one $R^o$ is substituted where each $R^o$ is a $C_6$ monocyclic aryl group, and
wherein when X is I, x is 2, and where X is S, x is 3.

* * * * *